United States Patent [19]

Bruckenstein et al.

[11] 4,315,753

[45] Feb. 16, 1982

[54] ELECTROCHEMICAL APPARATUS FOR SIMULTANEOUSLY MONITORING TWO GASES

[75] Inventors: Stanley Bruckenstein, Williamsville; John A. Kosek, Buffalo, both of N.Y.

[73] Assignee: The United States of America as represented by the Secretary of the Interior, Washington, D.C.

[21] Appl. No.: 177,978

[22] Filed: Aug. 14, 1980

[51] Int. Cl.³ .................... G01N 27/30; G01N 27/40; G01N 27/52

[52] U.S. Cl. ..................... 23/232 E; 204/195 M; 204/195 P; 422/83; 422/98

[58] Field of Search ........ 23/232 E, 232 R, 230 PC; 422/90, 98, 93, 83; 204/1 T, 195 M, 195 P, 195 R

[56] References Cited

U.S. PATENT DOCUMENTS

| | | | |
|---|---|---|---|
| 3,314,864 | 4/1967 | Hersch | 422/98 X |
| 3,837,808 | 9/1974 | Sugimoto et al. | 23/232 E |
| 3,909,204 | 9/1975 | Allen | 422/93 |
| 3,967,933 | 7/1976 | Etess et al. | 23/232 E |
| 3,977,836 | 8/1976 | Matsuda et al. | 23/232 R |
| 3,996,005 | 12/1976 | Topol | 23/232 E |

Primary Examiner—Ronald Serwin
Attorney, Agent, or Firm—Donald A. Gardiner

[57] ABSTRACT

The gas monitor of the present invention is capable of simultaneously determining the concentrations of two members of a family of oxygen-containing gases present in an air sample. The monitor utilizes a four electrode potentiostat (58, 70, 12, 14) including two indicating electrodes (58, 70) mounting in a single electrochemical cell (8) and immersed in an aqueous electrolyte (10). The air sample containing the two family members is initially passed to the first indicating electrode (58), where electroreduction of the first family member produces a first electrical current directly proportional to the concentration of the first family member in the sample. Thereafter, the gas sample is passed through an oxidizing means (4) interconnected between the two indicating electrodes (58, 70), where all of the second family member is converted into the first family member. Electroreduction of the first family member at the second indicating electrode (70) is then carried out to produce a second electrical current, which second current is electronically processed in analog measurement circuitry (74) to provide an indirect determination of the amount of the second family member present in the sample.

43 Claims, 13 Drawing Figures

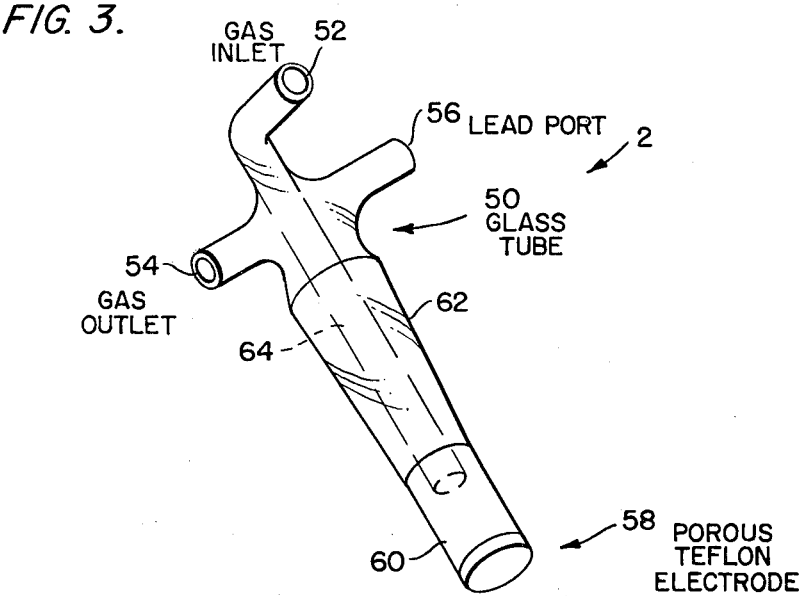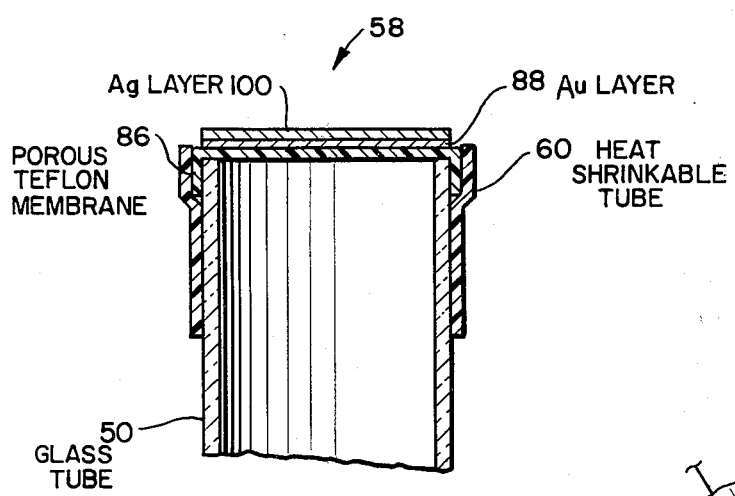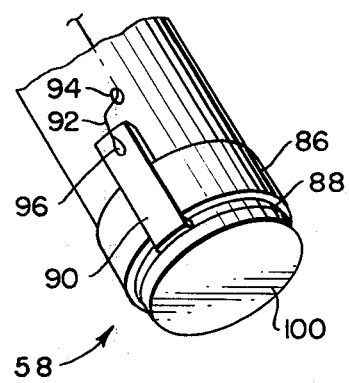

ELECTROCHEMICAL APPARATUS FOR SIMULTANEOUSLY MONITORING TWO GASES

TECHNICAL FIELD

This invention relates to monitors for quantitatively indicating the presence of gases and more specifically to a novel electrochemical gas monitor for simultaneously determining the concentrations of two different gases in a sample of ambient air.

BACKGROUND ART

In recent years, atmospheric pollution has become a source of major concern to government, industry and individuals alike. Even minute quantities of noxious gases and other chemical irritants present in the air can pose serious health and safety problems for persons exposed to the irritants. These problems may be area-wide or even regional in nature, as is often the case with automobile smog or heavy industrial pollution, or they may be confined to particular working environments such as chemical factories, oil, refineries or mining operations.

With regard to particular working environments, the Occupational Safety and Health Administration (OSHA) and other U.S. Governmental agencies have developed standards which set maximum allowable levels for exposure to toxic gases. Efforts to meet these standards, and indeed all attempts at controlling pollution from whatever source, quite obviously depend upon the ability to measure low pollutant levels accurately. Accordingly, numerous types of instruments for determining the presence and quantity of atmospheric pollutants have heretofore been proposed, manufactured and made available to the public.

Instruments for measuring the composition of the atmosphere utilize a wide variety of analytical techniques, including electrochemical techniques, gas chromatography, chemiluminescence, colorimetry and spectrophotometry. Electrochemical methods in particular have been the subject of extensive activity in the field of atmospheric analysis. The advent of modern integrated circuitry, coupled with the concomitant proliferation or reliable and inexpensive electronic components, has spurred the development of a wide variety of simple, compact measuring instruments with low power requirements. Recent examples of gas monitoring apparatus based on electrochemical methods can be found in U.S. Pat. No. 3,314,863, issued to Hersch et al on Apr. 18, 1967, and U.S. Pat. No. 3,821,090, issued to Topol et al on June 28, 1974.

Electrochemical cells for use in gas monitoring devices usually comprise three electrode potentiostats, which potentiostats include an indicating electrode, a reference electrode, and a counter or auxiliary electrode all immersed in a suitable electrolyte. Depending on the composition of the cell components and the value of the voltage applied across the indicating and counter electrodes, the gas being monitored is either electroreduced or electro-oxidized to produce an electrode current indicative of the amount of gas present.

As may be surmised, the effectiveness of any given electrochemical monitoring cell in detecting a specific type of gas is contingent upon obtaining the proper arrangement of cell components, and materials for forming the components must be carefully chosen in accordance with the electrochemical reaction desired. U.S. Pat. No. 4,152,233, issued to Chand on May 1, 1979, provides a representative list of compatible sensing electrodes, reference electrodes, counter-electrodes and electrolytes for each of a number of detectable gases. Modification of the structural features of these components can lead to further improvements in overall cell performance. For example, U.S. Pat. No. 4,057,478, issued to Bruckenstein et al on Nov. 8, 1977, teaches a means for constructing an electrode supporting substrate out of porous Teflon sheeting in order to provide increased stability during electrochemical cell operations. Additional prior art teachings have enabled the construction of gas monitors with improved accuracy and response time.

In spite of recent advances in the electrochemical cell art, many problems associated with the use of electrochemical cells to detect certain gases remain. One of the most serious of these problems results from the interfering presence of other species of gas in the sample of air being monitored. Devices of the type disclosed in the above-mentioned Hersch et al patent, which rely upon the oxidization of halogens in response to the passage of gaseous pollutants over a halide electrolyte, are susceptible to interference from chloride, bromine and organic sulfur compounds. Similarly, anodic oxidation of nitrogen dioxide to provide an electrochemical current as disclosed in Topol et al, also mentioned above, is subject to serious interference from both sulfur dioxide and carbon monoxide. It is thus often necessary to employ multiple filtration systems for removing interferents from a sample of gas prior to passage of the gas through the electrochemical monitoring cell. U.S. Pat. No. 3,677,708, issued to Harman III, et al on July 18, 1972, illustrates a multiple filtration system particularly useful with the Hersch et al device. These systems, however, inevitably add to the overall complexity and bulk of the monitor, and render the production of portable monitoring equipment more difficult.

Another obstacle to construction of truly practical atmospheric pollutant monitors arises out of the desire to measure more than one species of gas at a time. As disclosed in U.S. Pat. No. 3,622,487, issued to Chand et al on Nov. 23, 1971, and U.S. Pat. No. 3,763,025, issued to Chand on Oct. 2, 1973, prior art devices for detecting the combined presence of two oxidizable gases such as NO and $NO_2$ are known. Although many such devices are unable to distinguish between various atmospheric constituents and instead simply measure a cumulative pollutant total, other monitors do separate out and quantitatively indicate the individual noxious components present in a sample of air. The device disclosed in the above-mentioned Hersch et al patent, for instance, may be adapted to specifically determine ambient concentrations of both NO and $NO_2$. The electrochemical cell utilized by Hersch et al is primarily designed to measure $NO_2$, and any NO present in a gas sample will not interfere with the $NO_2$ analysis. On the other hand, the detection of NO in the electrochemical cell can only proceed after first routing the sample through a filter which removes all of the $NO_2$ initially present in the sample. Subsequently, the NO is chemically oxidized to $NO_2$ and passed through the cell to provide an indirect measurement of the amount of NO present in the sample. While Hersch et al accordingly provide a means for quantitatively isolating two oxidizable components of a sample of air, the requirement of a filtration step between the two component measurements significantly complicates the operation of the $NO/NO_2$ monitor.

Furthermore, even though Hersch et al use the same electrochemical cell structure to detect both NO and NO$_2$, there is nothing in the Hersch et al patent which suggests an arrangement suitable for simultaneous, as contrasted with sequential, monitoring of NO and NO$_2$. Consequently, in situations involving rapid fluctuations in the amount of noxious pollutants present in the atmosphere, the Hersch et al device would prove of little value in obtaining truly representative measurements of pollutant concentrations.

Prior art devices capable of simultaneously detecting multiple gaseous pollutants in an atmospheric sample are disclosed in U.S. Pat. No. 3,776,832, issued to Oswin et al on Dec. 4, 1973; U.S. Pat. No. 3,909,384, issued to Jasinski et al on Sept. 30, 1975; U.S. Pat. No. 4,001,103, issued to Blurton et al on Jan. 4, 1977; and U.S. Pat. No. 4,007,096, issued to Jasinski et al on Feb. 8, 1977. All of these prior art devices employ a separate electrochemical cell for each gas monitored, and the corresponding electronic circuitry must be expanded to include the electrical voltage supply, potential sequencing and detection functions necessary to the operation of each separate cell. In addition, the Blurton et al device requires an external filtration system for isolating the various noxious components of the air sample to be analyzed. Thus, regardless of their increased sensitivity to rapid changes in the atmosphere, none of the latter pollutant monitors is particularly suited to inexpensive manufacture in the form of a compact portable monitoring unit.

DISCLOSURE OF THE INVENTION

It is therefore a primary object of the present invention to provide a compact, reliable and inexpensive portable instrument unit for simultaneously monitoring the presence of atmospheric pollutants in an air sample.

It is an additional object of this invention to provide a compact, reliable and inexpensive portable instrument unit for simultaneously detecting each of at least two members of a family of oxygen-containing gases, which members are present in a sample of ambient air.

It is another object of the present invention to provide a compact, reliable and inexpensive portable instrument unit capable of accurately taking simultaneous measurements of individual NO and NO$_2$ concentrations in an ambient air sample.

It is a further object of the present invention to provide a portable gas monitor wherein simultaneous monitoring of the presence of more than one member of a family of oxygen-containing gases may be carried out using only one electrochemical cell.

It is yet another object of the present invention to provide a portable gas monitor employing a single electrochemical cell with two indicating electrodes positioned therein such that accurate and stable electroreduction techniques can be used to carry out simultaneous measurements of individual NO and NO$_2$ concentrations in an ambient air sample with a minimum of interference from other species of gas.

It is also an object of the present invention to provide an NO/NO$_2$ monitor wherein novel electronic circuit means are connected to two identical novel indicating electrodes mounted within a single electrochemical cell in order to generate accurate direct and indirect measurements, respectively, of the concentrations of NO$_2$ and NO in an ambient air sample.

These and other objects of the present invention are achieved by a gas monitoring instrument including a four electrode potentiostat formed from a reference electrode, an auxiliary or counter-electrode and two indicating electrodes mounted in a single electrochemical cell. Judicious selection of materials for and arrangement of the various electrodes permits simultaneous determination of the amounts of two members of a family of oxygen-containing gases present in an air sample. The air sample containing the two family members is initially passed to the first indicating electrode, where one of the family members is measured. Thereafter, the gas sample is passed through an oxidizing means interconnected between the two indicating electrodes, where all of the second family member is converted into the first family member. Indirect measurement of the second family member is subsequently carried out at the remaining indicating electrode. Provision of the oxidizing means enables the same electrode structure to be employed in both indicating electrodes.

When NO and NO$_2$ are the family members to be detected, the two indicating electrodes may each consist of a hydrophilic porous Teflon membrane upon which layers of gold and silver have been successively deposited. Sulfuric acid is used as the supporting electrolyte. The first "silver porous Teflon" electrode serves to electroreduce nitrogen dioxide present in a sample of gas passing through the monitor, thereby providing a first electrical current directly proportional to the concentration of nitrogen dioxide present in the sample. All of the nitric oxide originally present in the gas sample is then converted to nitrogen dioxide by the oxidizing means, and subsequent electroreduction at the second "silver porous Teflon" electrode provides a second electrical current. In addition to the nitrogen dioxide formed from the originally present nitric oxide, however, the gas sample reaching the second "silver porous Teflon" electrode also contains oxidized reduction products and unreduced nitrogen dioxide from the first "silver porous Teflon" electrode. These additional gases contribute unwanted components to the current generated by the second "silver porous Teflon" electrode. Consequently, the NO/NO$_2$ monitor of the present invention employs novel circuit means to subtract a fractional amount of the first or NO$_2$ indicating current from the current generated by the second or NO indicating electrode, thereby providing a net current proportional to the concentration of NO present in the air sample.

BRIEF DESCRIPTION OF THE DRAWINGS

The various features, objects and advantages of the present invention will become more apparent from the following Brief Description of the Drawings.

FIG. 3 is a perspective view of an indicating electrode assembly constructed in accordance with the present invention;

FIG. 4A is an enlarged cross-sectional view of the electrode portion of the indicating electrode assembly illustrated in FIG. 3;

FIG. 4B is an enlarged perspective view of the electrode portion of FIG. 4A, showing the indicating electrode lead connections;

BEST MODE FOR CARRYING OUT THE INVENTION

Figure 1:
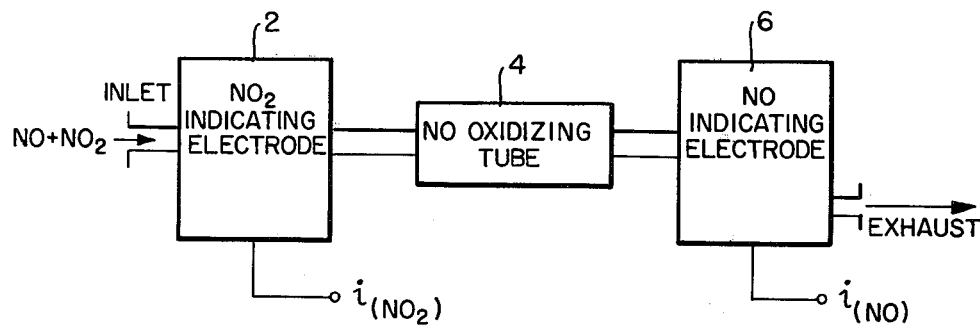
FIG. 1 is a block diagram illustration of a process for carrying out an NO/NO$_2$ analysis in accordance with the present invention.

As will now be described in detail, the preferred embodiment of a gas monitor constructed in accordance with the present invention is designed to measure NO and $NO_2$. It is nevertheless to be understood that the apparatus of the present invention can be suitably modified to simultaneously monitor any desired number of compounds in the nitrogen oxide family. Moreover, the basic concepts of the present invention can be readily adapted to provide an apparatus for simultaneously monitoring the individual members of other families of oxygen-containing gases and vapors such as those containing compounds of carbon, sulfur and hydrogen. In this regard, the term family of oxygen-containing gases means the members of a related group of gases, each of which members has a common atom such as nitrogen, carbon or sulfur in combination with one or more oxygen atoms. At least one of the members to be measured must be electrochemically detectable and the remaining members to be measured must be chemically convertible to the electrochemically detectable member. Exemplary members of such a family based on nitrogen might include NO and $NO_2$, whereas a family based on carbon might include CO and $CO_2$ and a family based on sulfur might include $SO_2$ and $SO_3$.

Returning to a discussion of an $NO/NO_2$ monitor, experimentation has demonstrated that the electroreduction of $NO_2$ using a "silver porous Teflon" electrode (hereinafter referred to as a silver PTE) constructed in accordance with the present invention and immersed in an aqueous acid supporting electrolyte yields an accurate and stable electrical current indicative of $NO_2$ concentration. Further analysis reveals that the overall stoichiometry of the electroreduction reaction involved is dependent upon the flow rate of the gas sample past the silver PTE. For example, the initial step in the reduction process has been proposed as:

$$NO_2 + e \rightarrow NO_2^- \tag{1}$$

The amount of relatively unstable $NO_2^-$ generated during Reaction 1 and otherwise available for further electroreduction, however, is decreased at high sample flow rates in accordance with the chemical reaction:

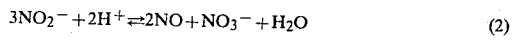

$$3NO_2^- + 2H^+ \rightleftharpoons 2NO + NO_3^- + H_2O \tag{2}$$

High flow rates apparently cause NO generated during Reaction (2) to be rapidly removed from the site of the reduction, thereby maximizing the conversion of $NO_2^-$ to NO and removing the $NO_2^-$ from the reduction environment. As a net result, when high flow rates are present the one electron reduction suggested by Reaction (1) becomes the predominant electroreduction mechanism.

At lower flow rates, Reaction (2) is not as important and Reaction (1) may be seen as the first step in a two step electroreduction. The second step may be written as:

$$NO_2^- + 2H^+ + e \rightarrow NO + H_2O \tag{3}$$

Combining Reactions (1) and (3) yields the Reaction:

$$NO_2 + 2H^+ + 2e \rightarrow NO + H_2O \tag{4}$$

Accordingly, the predominant electroreduction mechanism at lower flow rates may be characterized by the two electron reduction indicated in Reaction (4).

The relationship between reduction current and $NO_2$ concentration using a silver PTE in an aqueous acid supporting electrolyte has been found to be linear relative to $NO_2$ concentration. Moreover, few volatile species other than $NO_2$ generate an electrochemical response in a silver PTE. Hydrogen sulfide, which decreases the sensitivity of a silver PTE by reacting with the electrode surface to form $Ag_2S$, is in fact the only serious interferent likely to be encountered in monitoring environments. Thus, proper functioning of a monitor employing silver PTE's may be easily maintained through the use of a simple filter for removing hydrogen sulfide from a sample of monitored gas before the gas reaches the silver PTE.

As previously noted, it is often desirable to obtain a determination of the amount of NO as well as $NO_2$ present in an ambient air sample. Prior art teachings frequently refer to electro-oxidation techniques for use in NO analysis, but experimentation with the electro-oxidation of NO has indicated that the presence of a number of other oxidizable volatile species of gas in the ambient air sample seriously interfers with an NO analysis based on an electro-oxidization process. Consequently, if the bulk, complexity and expense of sophisticated multiple filtration systems for pre-conditioning ambient air samples is to be avoided in an $NO/NO_2$ monitor, an alternative method for measuring NO concentrations, compatible with $NO_2$ electroreduction, must be employed.

The present invention provides such an alternative method in the form of a process for indirectly measuring NO concentrations in ambient air, wherein NO present in an ambient air sample is chemically oxidized to produce $NO_2$ for subsequent analysis via silver PTE electroreduction. FIG. 1 illustrates the basic concept involved. An air sample containing both NO and $NO_2$ enters a first indicating electrode assembly 2 containing an $NO_2$ indicating electrode comprising a first silver PTE. $NO_2$ present in the sample is electroreduced at the $NO_2$ indicating electrode to produce a current $i(NO_2)$ proportional to the amount of $NO_2$ present. The air sample next passes through an oxidizing tube 4, where all of the NO in the sample is chemically oxidized to $NO_2$. Thereafter, the $NO_2$ produced by the chemical oxidation of NO is electroreduced in a second indicating electrode assembly 6 containing an NO indicating electrode comprising a second silver PTE which provides a current $i(NO)$. The terminology "NO indicating electrode" does not, of course, apply literally, in view of the fact that indicating electrode assembly 6 actually operates to electroreduce $NO_2$ as a means of obtaining the indirect measure of NO concentration. Nevertheless, for the sake of clarity and consistency all monitor components associated with the NO indicating function of the monitor will hereinafter be referred to as NO indicating components.

Referring back to Reactions (2) and (4), it can be seen that regardless of sample flow rate, a certain amount of NO will be produced in the first indicating electrode assembly 2 as a result of the electroreduction of $NO_2$. This newly-generated NO is oxidized in oxidizing tube 4 along with the originally-present NO, and subsequently contributes an unwanted component to i(NO). In addition, studies have shown that only about 10% of the $NO_2$ originally present in the ambient air sample is actually electroreduced in indicating electrode assembly 2, and the electroreduction of the remaining non-reduced $NO_2$ in indicating electrode assembly 6 contributes a second unwanted component to i(NO). Consequently, as described more fully hereinbelow, suitable electronic circuitry must be employed to remove these unwanted current components in order to obtain from i(NO) a current proportional to the amount of NO originally present in the sample.

Figure 2:
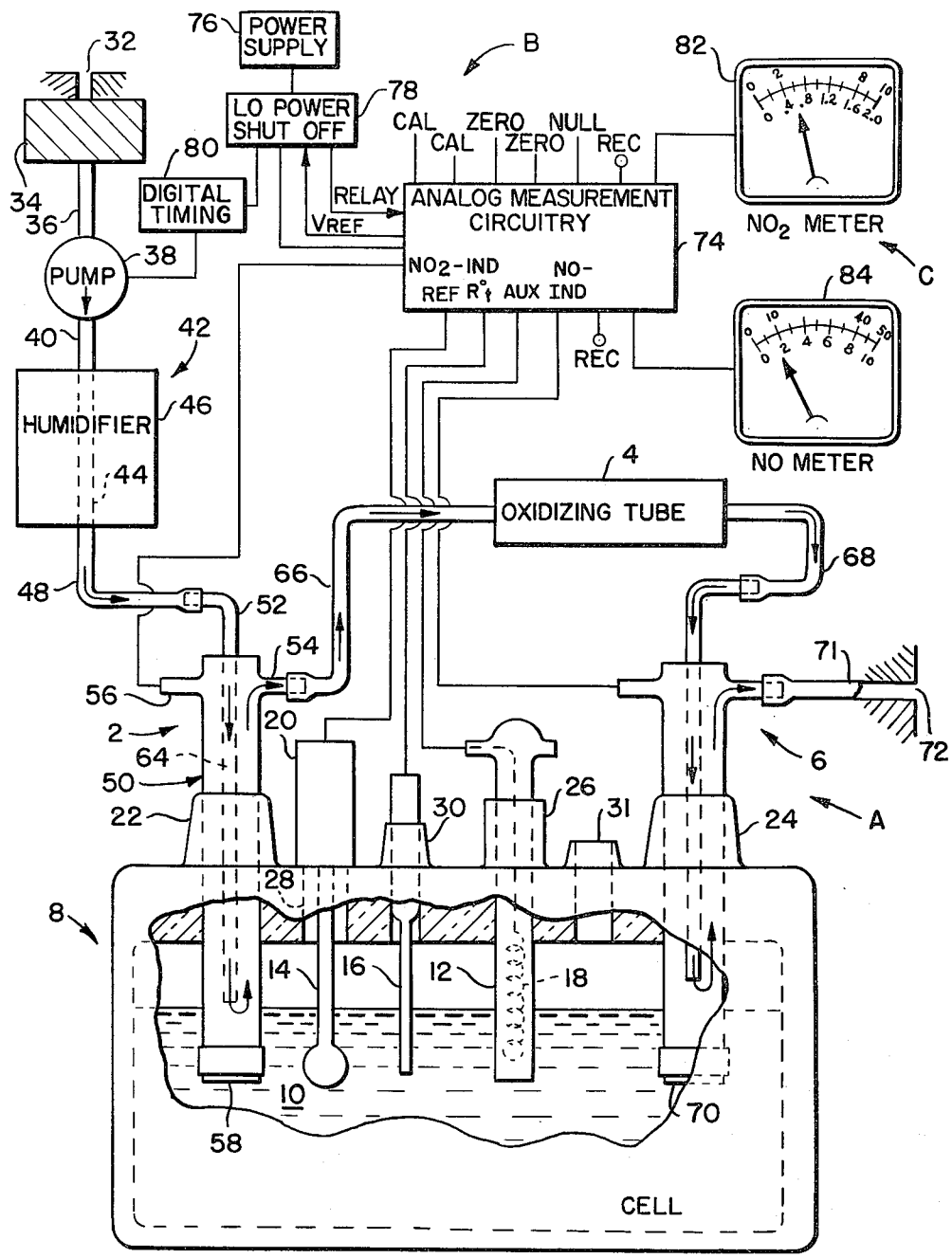
FIG. 2 is a diagrammatic representation showing the arrangement of the various electrochemical components in an NO/NO$_2$ monitor of the present invention.

Turning to FIG. 2, a schematic layout of a gas monitor employing the principles set out in connection with FIG. 1 can be seen. The $NO/NO_2$ monitor of the present invention generally comprises a detection system A, electronic measurement and power supply system B and a display system C. An electrochemical cell 8 filled with a suitable electrolyte 10 provides the environment for the desired reduction reactions. In the preferred embodiment, cell 8 is constructed of plexiglass, but any suitably durable material may be used. Electrolyte 10 is preferably an aqueous acid such as 0.5 M $H_2SO_4$. $1 \times 10^{-3}$ M $NH_2SO_3H$ may be added to the sulfuric acid to prevent accumulation of $NO_2^-$ in the solution.

The two indicating electrode assemblies 2 and 6 are mounted in cell 8 and immersed in electrolyte 10. The cell components additionally include an auxiliary or counter electrode 12, a reference electrode 14 and a thermistor 16. Auxiliary electrode 12 consists of a coil of gold wire 18 fitted in a glass tube and separated from the electrolyte solution by a medium porosity fritted glass disc (not shown). Reference electrode 14, which is inserted directly into supporting electrolyte 10, preferably consists of a very high resistance glass pH electrode (such as Model No. 13-639-205 available from Fisher Scientific Co.). The glass composition of the reference electrode imparts long term operating stability to the cell, but in order to compensate for the high impedance of glass, an operational amplifier enclosed in a piece of copper tubing 20 is mounted directly on the electrode casing. Thermistor 16 is employed to provide temperature compensation for the electronic measurement circuitry and power supply system B.

Five mounting ports 22, 24, 26, 28, 30 formed in reference cell 8 respectively receive the indicating electrode assemblies 2 and 6, auxiliary electrode 12, reference electrode 14 and thermistor 16. Heat shrinkable polyethylene tubing (not shown) can be used to secure the electrode assemblies in position within the mounting ports. If desired, an additional port 31 can be formed in cell 8 to provide "breathing" capability should the pressure of the surrounding atmosphere change. Port 31, if employed, is covered with a porous Teflon membrane (not shown).

The air sampe to be measured enters the $NO/NO_2$ monitor via entry port 32 and is pumped through filter unit 34 by sample pump 38. Sample pump 38 may be a low powered diaphram pump (such as Bendix Corp. Model No. P-N2417110-0003 available from Bendix Environmental Corp., Baltimore, MD) operated at a flow rate of 600 $cm^3$/min. Filter unit 34 is designed to remove hydrogen sulfide gas from the sample stream. Silver nitrate is particularly effective for this purpose, and can be utilized as the filtering media.

From filter 34, the sample stream passes through conduit 36, sample pump 38 and conduit 40 into humidifier 42. Conduits 36 and 40, and all subsequent monitor conduits, may be formed from any suitable material, but in the preferred embodiment Teflon tubing is employed.

Humidifier 42 is comprised of a short link of porous Teflon tubing 44 supported in a plexiglass container 46. The container is filled with a $1 \times 10^{-3}$ M sulfamic acid solution to prevent $NO_2^-$ build-up in the humifier.

The sample stream next passes through conduit 48 to the first indicating electrode assembly 2, shown in greater detail in FIG. 3. Indicating electrode assembly 2 includes a glass tube 50 having a gas inlet port 52, a gas outlet port 54 and an electrode lead port 56 at one end thereof. An $NO_2$ indicating electrode 58 comprised of a silver PTE is mounted at the opposite end of tube 50 for contact with electrolyte 10 and is secured to the tube by a piece of heat shrinkable polyethylene tubing 60. The central portion 62 of glass tube 50 may be tapered to insure a proper fit in mounting port 22. The sample stream in conduit 48 enters indicating electrode assembly 2 through inlet port 52 and is introduced to the $NO_2$ indicating electrode 58 via an interior tube 64 in fluid communication with inlet 52. The porosity of a silver PTE constructed in accordance with the present invention is such that the gases present in the sample stream diffuse through the $NO_2$ indicating electrode 58 to the electrode-electrolyte interface, where electroreduction of $NO_2$ takes place. The $NO_2$ indicating electrode, however, is impervious to the reverse passage of the electrolyte into tube 50. Current $i(NO_2)$ generated during the electroreduction reaction is removed from the electrode-electrolyte interface by an electrode lead $NO_2$-IND which passes through glass tube 50 and electrode lead port 56.

The sample stream, which now contains both reduction products and unreduced $NO_2$ in addition to the NO present in the original sample, exits indicating electrode assembly 2 via gas outlet port 54 and passes through conduit 66 to the oxidizing tube 4. Oxidizing tube 4 comprises a short link of glass tubing filled with $Cr_2O_3$ oxidant solidly supported on crushed fire brick particles (Sil-O-Cell C-3, available from Johns Manville Co.). The oxidant in tube 4 oxidizes all of the NO present in the sample stream to $NO_2$.

Upon leaving oxidizing tube 4, the sample stream flows through conduit 68 to the second indicating electrode assembly 6 mounted in electrochemical cell 8. Indicating electrode assembly 6, which includes an NO indicating electrode 70 formed from a second silver PTE, is identical to indicating electrode assembly 2 and reference is made to the specification describing FIG. 3 for further details on the construction and function thereof. The current i(NO) generated as a result of the electroreduction occurring in indicating electrode assembly 6 is removed from assembly 6 by an electrode lead NO-IND and processed in electronic measurement and power supply system B to provide a measure of NO concentration. The sample stream then exits indicating electrode assembly 6 and is conducted through conduit 71 to exhaust port 72, where the sample stream is discharged to the atmosphere.

Electronic measurement and power supply stream B includes analog measurement circuitry 74, a power supply 76 with a low-power shut-off control 78, and a digital timing circuit 80 for controlling the operation of the sample pump 38. Analog measurement circuitry 74 receives the NO$_2$-IND input from indicating electrode assembly 2, the NO-IND input from indicating electrode assembly 6, an AUX input from auxiliary electrode 12, a REF input from reference electrode 14 and an $R_t°$ input from thermister 16. Calibration (CAL) and zeroing (ZERO) operations may be performed on circuitry 74, and a NULL operation is carried out to remove the aforementioned unwanted components in the NO-IND signal.

The NULL operation is particularly important, inasmuch as the unwanted components in the electroreduction current i(NO) generated in indicating electrode assembly 6 would otherwise introduce a serious error factor into the operation of the NO/NO$_2$ monitor of the present invention. As previously discussed, the sample stream fed to oxidizing tube 4 from indicating electrode assembly 2 contains NO as an NO$_2$ reduction product, as well as the NO originally present in the sample. Consequently, both the amount of NO entering oxidizing tube 4 and the amount of NO$_2$ generated therein substantially represent the combined amounts of original NO and reduced NO$_2$. When further account is taken of the remaining un-reduced NO$_2$ in the sample stream entering and leaving the oxidizing tube, it can be seen that the total amount of NO$_2$ reaching indicating electrode assembly 6 and the subsequently produced electroreduction current is actually proportional to the cumulative concentration of NO and NO$_2$ initially entering the monitor. Analog measurement circuitry 74 compensates for this distortion by subtracting a predetermined fractional amount of the current i(NO$_2$) generated in indicating electrode assembly 2 from the current i(NO) generated in indicating electrode assembly 6, thus providing a corrected current signal which accurately measures only the ambient NO concentration in the sample stream.

Display system C includes a meter 82 for indicating NO$_2$ concentration in either a range from 0 to 2.0 ppm or a range from 0 to 10 ppm. Similarly, meter 84 indicates NO concentration in either a range from 0 to 10 ppm or 0 to 50 ppm. If desired, recording jacks (REC) may also be furnished for the purpose of supplying data signals to a recording device (not shown).

The method of constructing a silver PTE will now be described in detail. Reference is made to FIGS. 4A and B which respectively illustrate a cross-sectional view of NO$_2$ indicating electrode 58 and the electrode lead connection for indicating electrode assembly 2. It is again understood that the method to be described is equally applicable to either the silver PTE used as NO$_2$ indicating electrode 58 or the silver PTE used as NO indicating electrode 70.

Turning to FIG. 4A, a 2"×2" piece of hydrophilic porous Teflon membrane 86 (such as Gore-Tex Number S10363, 4 mil. thick, available from W. L. Gore and Associates, Elkton, Md.) is stretched tightly over the end of glass tube 50. Three drops of gold resinate are placed on the porous Teflon membrane 86 and spread over the entire surface thereof with a small brush. Gold resinate (such as Number 8300 available from the Hanovia Division of Engelhardt Industries, East Newark, N.J.), containing 28% gold suspended in an organic matrix, may be used for this purpose. The resinate is cured by applying heat from a heat gun at a distance of approximately six inches, whereupon the resinate first turns black and then dull gold in color. The gold coating and curing procedure is repeated two more times, and the three coats of resinate thus applied together form a layer of gold, designated 88 in FIG. 4A, on the porous Teflon membrane.

As seen to best advantage in FIG. 4B, a one-half inch wide stripe of gold resinate is also painted down one side of the glass tube 50 to form a contact pad 90 for making electrical contact with the electrode surface. A piece of 24 gauge gold wire 92 is inserted into the electrode lead port 56 of tube 50, passed down the tube and then threaded through an aperture 94 formed in the wall of glass tube 50 to connect with the contact pad 90. After wire 92 is passed therethrough, aperture 94 in the side of the glass tube 50 is epoxied to prevent the escape of gas from the tube and to prevent leakage of electrolytic solution into the indicating electrode assembly once the assembly is installed in electrochemical cell 8.

Wire 92 is then pressed against contact pad 90 and the resistance therebetween measured. If the resistance is greater than 5 ohms, the gold resinate is cured for a few minutes more. If the resistance between the wire and the contact pad is still greater than 5 ohms, another thin coat of gold resinate is applied. When a satisfactory resistance of less than 5 ohms has been achieved, a piece of Teflon tape (not shown) (such as Pipe Thread Tape available from W. L. Gore and Associates, Elkton, Md.) may be wrapped tightly around the end of the glass tube to hold wire 92 against contact pad 90. If desired, the end 96 of gold wire 92 may be flattened to facilitate contact with pad 90. The other end of gold wire 92 may be force fitted into a jack (not shown) (such as a Cambion Teflon-insulated pin jack Model No. 450-4352-01-03, available from Cambridge Thermionic Corp., Cambridge, Mass.). The jack, which provides a contact means for electrically connecting gold wire 92 to the appropriate electrode or IND lead, is pressed into the electrode lead port 56 after the port is filled with a butyl rubber caulking compound.

Heat shrinkable polyethylene tubing 60 is shrunk around the end portion of the glass tube 50 to clamp the porous Teflon membrane 86 against the tube, thus securing the now partially-completed silver PTE to the rest of the indicating electrode assembly. If desired, epoxy can also be used to attach membrane 86 to the glass tube.

The indicating electrode assembly may next be tested for porosity by connecting either the gas inlet port 52 or the gas outlet port 54 to a water aspirator while plugging the remaining gas port. Acetone is drawn through the electrode surface. If the acetone does not pass through membrane 86, or passes through very slowly, the silver PTE is judged non-porous and must be rebuilt. Following porosity testing the partially-completed silver PTE is baked in a 180° C. oven under vacuum conditions for one hour. Baking helps to cure any uncured resinate, and also serves to remove any excess acetone from the pores of the Teflon membrane.

Gold layer 88 of the silver PTE is subsequently treated using the electrode conditioning circuit illustrated in FIG. 5A. Two partially-completed silver PTE's are placed in an electrochemical cell 98 containing 1 M HClO₄ and respectively connected to points A and B in the feedback loop of amplifier A1. Amplifier A3 is energized to generate a square wave with a frequency of 0.1 Hz. Amplifier A5 adjusts the symmetry of the square wave around zero current, while transistors Q1 and Q3 boost the current supplied by amplifier A1. The current magnitude is generally set at plus or minus 50 mA, but may be adjusted via potentiometer P1. The output waveform of the electrode conditioner is shown in FIG. 5B. Values of the circuit resistors and capacitors are listed in Table I.

Figure 5A:
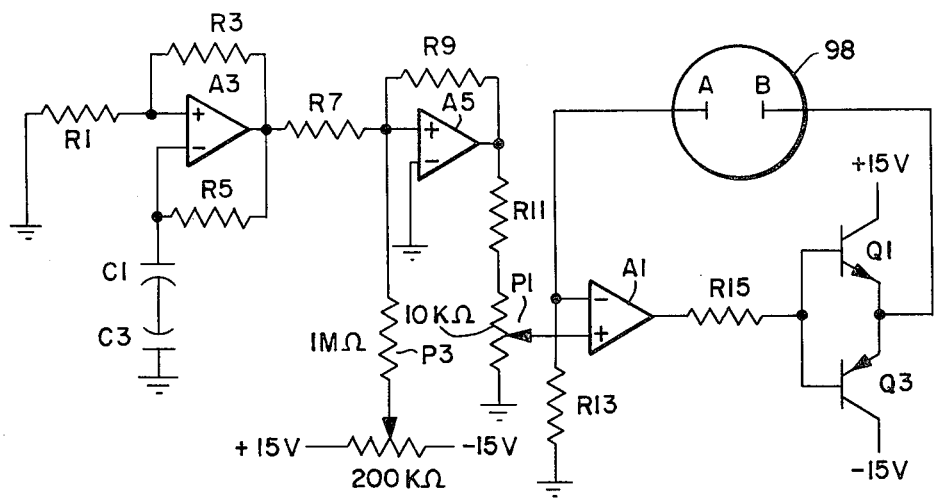
FIG. 5A is a circuit diagram of an electrode conditioning circuit for use in constructing a silver porous Teflon electrode.
Figure 5B:
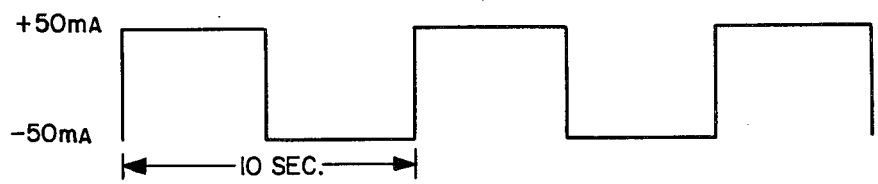
FIG. 5B illustrates the current output waveform of the circuit disclosed in FIG. 5A.

TABLE I
Values of Circuit Components in FIG. 5A

| Component | Value | Component | Value |
|---|---|---|---|
| R1 | 100KΩ | R11 | 2.7KΩ |
| R3 | 100KΩ | R13 | 10Ω |
| R5 | 470Ω | R15 | 100Ω |
| R7 | 10KΩ | C1 | 8μf |
| R9 | 10KΩ | C3 | 8μf |

The partially-completed silver PTE's are conditioned for at least 8 hours, during which time nitrogen is blown over the back side of the porous Teflon membrane 86.

Silver plating is the final step in the electrode construction process. Following treatment in the electrode conditioning circuit, each partially-completed silver PTE is immersed in a 0.1 M AgNO₃/1 M HNO₃ electrolytic solution and potentiostated at 0.0 volts for three minutes. The potentiostat may employ an auxiliary electrode formed from a coiled platinum wire separated from the bulk electrolyte by a glass frit, and a glass pH electrode may be used as the reference electrode. The electrolytic solution is stirred during the plating step by means of a stirring bar and magnetic stirrer. The solution need not be deoxygenated before use, nor is it necessary to make any provisions to exclude oxygen from the plating system. After three minutes of potentiostating, a layer of silver, designated 100 in FIG. 4A, is formed over gold layer 88. The silver PTE is removed from the AgNO₃ solution and rinsed with triply distilled or Milli-Q water to complete the electrode construction process.

Figure 6:
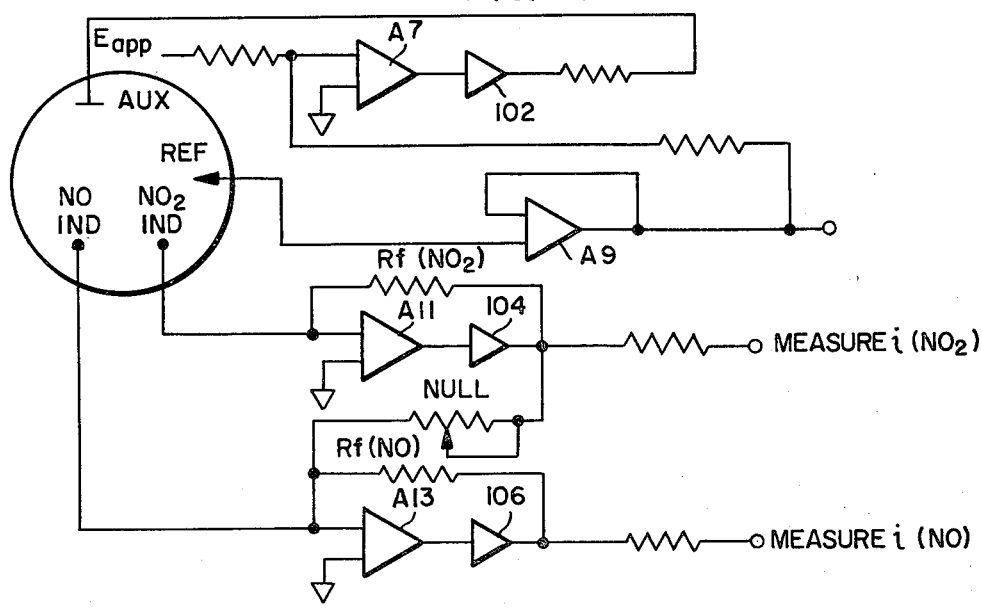
FIG. 6 is a schematic representation of the four electrode potentiostat employed in the present invention.

FIG. 6 provides a basic schematic illustration of the potentiostat arrangement employed in the NO/NO₂ monitor of the present invention. An auxiliary electrode potential is maintained at a value $E_{app}$ by amplifier A7, with feedback from the reference electrode through amplifier A9. The working potential of the NO₂ and NO indicating electrodes 58 and 70 are both held at a constant value with respect to reference electrode 14. Thus, potential cycling is not required and the potentiostat may easily be operated in a continuous sampling mode. The optimum working potential for the NO₂ and NO indicating electrodes 58 and 70 is one at which the background response to the two electrodes is small while the response to the electroreduction of NO₂ is large. In the preferred embodiment of the NO/NO₂ monitor of the present invention, a potential of −0.24 volts relative to the reference electrode is employed as the working potential because such a potential is characterized by relatively stable electrode sensitivity to both NO₂ and background current. Moreover, the potential of −0.24 volts is not too close to the potential for silver oxidation, and the silver PTE's which form electrodes 58 and 70 will not be appreciably consumed over long periods of monitor usage.

Each indicating electrode 58, 70 serves as a cathodic electrode in the electrochemical sense. Accordingly, with the support of electrolyte 10 reduction of NO₂ takes place at each indicating electrode and electrical current is generated between the indicating electrodes 58, 70 and auxiliary electrode 12. NO₂ indicating current i(NO₂) from indicating electrode assembly 2 is amplified by NO₂ current measuring amplifier A11 across resistor $R_f$(NO₂). NO current measuring amplifier A13 and resistor $R_f$(NO) are used to amplify NO indicating current i(NO) from indicating electrode assembly 6. As previously discussed, a NULL operation, using a potentiometer as hereinafter more fully described, is performed on i(NO) using the amplified NO₂ indicating current. Current boosters are provided at 102, 104 and 106.

Figure 7:
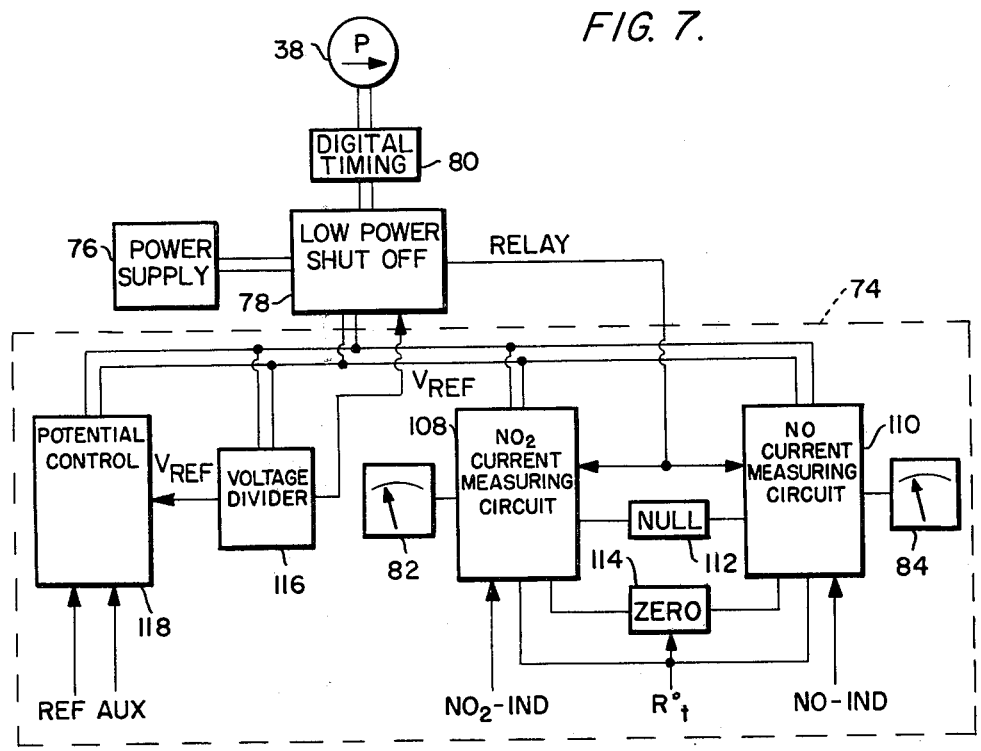
FIG. 7 is a block diagram of the measuring and indicating circuitry of the present invention.

A block diagram of the electronic measurement and power supply system B is shown in FIG. 7. Analog measurement circuitry 74 includes circuits 108 and 110 for respectively measuring NO₂ and NO indicating currents from indicating electrode assemblies 2 and 6. NO₂ and NO current measuring circuits 108 and 110 are interconnected via a compensating circuit 112 which provides the aforementioned NULL function. Circuit 114 furnishes zeroing capability for the two current measuring circuits. The working potential of the monitor is obtained from voltage divider 116, while potential control for the electrochemical cell 8 is achieved by potential control circuit 118 in combination with the reference and auxiliary electrodes. Power for the monitor is supplied by power supply 76. Low power shut-off control 78 track power supply 76 and shuts the monitor off whenever the power supply voltage falls below a preset level. Digital timing circuit 80 outputs control signals to operate the sample pump 38 in either a manual or continuous sampling mode. Meter 82 displays NO₂ concentrations in response to signals from NO₂ current measuring circuit 108, while meter 84 displays NO concentrations in response to signals from NO current measuring circuit 110. Meter 82 may also be used to display the state of the monitor power supply.

Figure 8B:
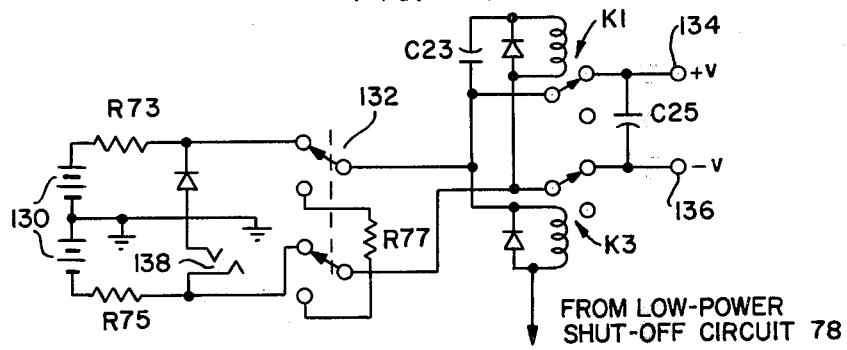
FIGS. 8A, 8B and 8C are detailed circuit diagrams illustrating the monitor circuitry of the present invention.
Figure 8C:
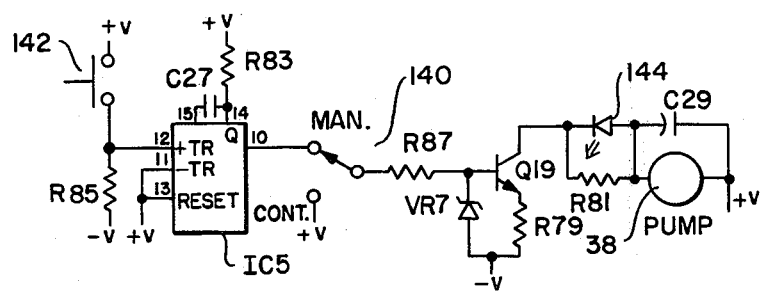
Figure 8A:
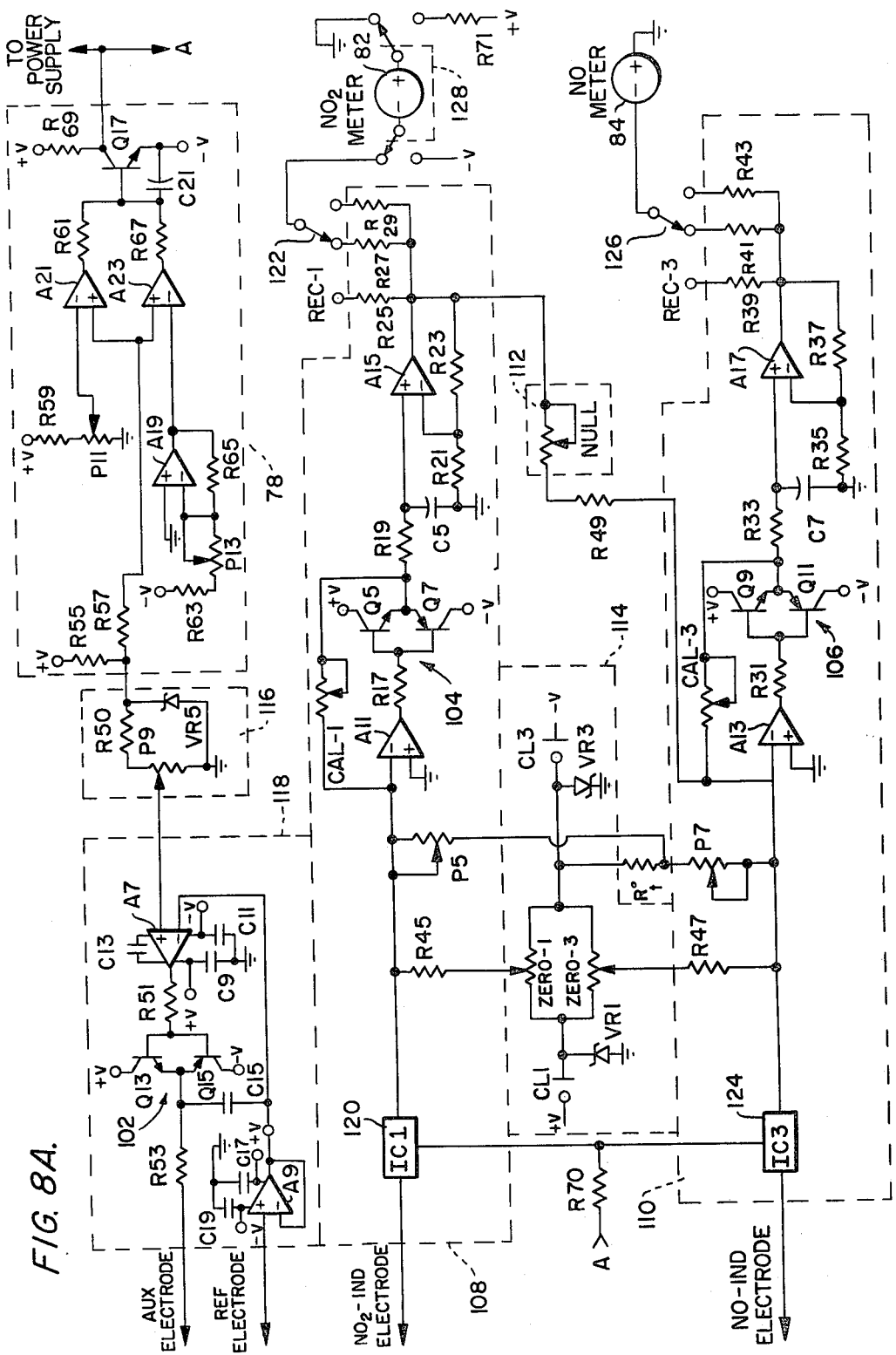

Turning to FIGS. 8A, 8B and 8C, a detailed circuit diagram of the electronic measurement and power supply system B is illustrated. As seen to best advantage in FIG. 8A, NO₂ current measuring circuit 108 employs the NO₂ current measuring amplifier A11 to provide a proportional representation of the current i(NO₂) generated during the electroreduction of NO₂ in indicating electrode assembly 2. Amplifier A11 receives the NO₂ indicating current from indicating electrode assembly 2 through a solid state relay 120, which relay functions in response to the operation of low power shut-off control 78 to remove NO₂ indicating electrode 58 from the NO₂ current measuring circuit as explained more fully hereinbelow. Current booster 104 in the form of transistors Q5 and Q7 boosts the total current available from the NO₂ current measuring amplifier A11 to a maximum of 100 mA. The feedback resistance CAL-1 (e.g., $R_f$(NO₂)) simultaneously serves as a means for calibrating the NO₂ current measuring amplifier. Circuit 108 also includes follow amplifier A15 and a resistor network R25–R29 at the output of amplifier A15. The resistor network is operated by NO₂ range switch 122 to provide scaling for the NO₂ meter 82. R27 is connected to the 0–2 ppm NO₂ concentration range output and R29 is connected to the 0–10 ppm NO₂ concentration range output. R25 is connected to an NO₂ recorder output jack REC-1 for supplying an output signal to a recording device.

NO current measuring circuit 110 includes a solid state relay 124, NO current measuring amplifier A13, current booster 106 in the form of booster transistors Q9 and Q11, feedback and calibrating resistance CAL-3 (e.g., $R_f(NO)$), follower amplifier A17 and resistor network R39–R43, all of which function in a manner analogous to the components of $NO_2$ current measuring circuit 108. In accordance with the setting of NO range switch 126, resistor R41 is connected to the 0–10 ppm NO concentration range output while resistor R43 is connected to the 0–50 ppm NO concentration range output. An NO recorder output jack REC-3 is connected to resistor R39.

Compensating circuit 112 basically comprises a NULL potentiometer connected between the output of follower amplifier A15 in $NO_2$ current measuring circuit 108 and the summing point of the NO current measuring amplifier A13. The purpose of the NULL potentiometer is to remove the unwanted components of i(NO) generated at indicating electrode assembly 6. These unwanted components result from the electroreduction of any originally-present $NO_2$ not electroreduced in indicating electrode assembly 2 and the electroreduction of $NO_2$ formed from the oxidation of NO produced during the electroreduction of $NO_2$ in assembly 2. The NULL potentiometer is set during initial calibration of the monitor by supplying a sample of pure $NO_2$ to the monitor entry port 32 and adjusting the NULL potentiometer until the meter reading on the NO meter 84 is zero. Thereafter, whenever the monitor is used a fractional amount of the $NO_2$ indicating current will automatically be subtracted by the NULL potentiometer from the NO indicating current to provide a corrected current, the magnitude of which represents the component of i(NO) due solely to the NO originally present in the sample stream being monitored. This corrected current is then amplified by NO current measuring amplifier A13 and displayed on NO Meter 84 to provide an accurate indication of the amount of NO present in the sample.

Circuit 114 employs two zero adjustment potentiometers ZERO-1 and ZERO-3. One side of each zero adjustment potentiometer is connected to the positive power supply through constant current diode CL1 while the other side of each zero adjustment potentiometer is connected to the negative power supply through constant current diode CL3. The constant current diodes make the outputs of the zero adjustment potentiometers less susceptible to fluctuations in the voltage supply. 2.1 volt zener diodes VR1 and VR3 respectively connected between ground and CL1 and CL3 insure a constant offset voltage over the entire range of usable power supply voltage.

Zeroing of the monitor is accomplished by suitable adjustment of the ZERO-1 and ZERO-3 potentiometers. Resistor R45 connected between the wiper of the ZERO-1 potentiometer and the summing junction of the $NO_2$ current measuring amplifier A11 provides for the injection of a current opposite in sign and equal in magnitude to the sum of the background current and the current through thermistor $R_t^o$, thereby completing the zero offset correction. Resistor R47 performs the same function for the NO current measuring amplifier A13.

Thermistor $R_t^o$ (10 Kohm at 25° C.) is employed to compensate for the temperature dependent background current in $NO_2$ and NO current measuring circuits 108 and 110. One terminal of the thermistor is connected to both potentiometers P5 and P7 while the other terminal of the thermistor is connected to the −2.1 volt side of the zero adjustment potentiometers ZERO-1 and ZERO-3.

The value of the settings for potentiometers P5 and P7 are determined by disconnecting the thermistor $R_t^o$ and the zero adjustment potentiometers ZERO-1 and ZERO-3 from the $NO_2$ and NO current measuring amplifiers A11 and A13. The NULL potentiometer is also disconnected. The monitor is then thermostated at several temperatures between the limits of projected field use (i.e., 5°–35° C.). The monitor exhaust port 72 is connected to entry port 32 in order to recirculate the sampled air and bring the air to the temperature of the monitor. Such recirculation also assures that the air sample is free of NO and $NO_2$. Thermistor values and the voltage $E_o$ across current measuring amplifiers A11 and A13 are then measured. Where the $NO/NO_2$ monitor circuitry employs the circuit components as designated in Table III below, columns 2, 3 and 4 of Table II report typical values for $R_t^o$, $E_o^{NO}$ and $E_o^{NO_2}$.

TABLE II

| Temp (°C.) | $R_t^o$ (KΩ) | Zero Calibration Data | | | |
|---|---|---|---|---|---|
| | | $E_o^{NO}$ (V) | $E_{20}^{NO_2}$ (V) | $i_o^{NO}$ (μA) | $i_o^{NO_2}$ (μA) |
| 10 | 12.21 | −0.069 | −0.226 | 9.09 | 5.37 |
| 20 | 9.17 | −0.099 | −0.312 | 13.04 | 7.41 |
| 30 | 7.19 | −0.114 | −0.398 | 15.02 | 9.45 |

For each current measuring amplifier the background current $i_o$ can be calculated at each temperature from a straightforward application of Ohm's Law:

$$i_o = \frac{E_o}{R(CAL)} \quad (5)$$

where R(CAL) is the resistance (equal to the feedback resistance) of the appropriate calibration adjustment potentiometer CAL-1 or CAL-3. Typical values of $i_o$ at various temperatures are given at columns 5 and 6 of Table II.

The value of $R_x$, the resistor in series with $R_t^o$ required to produce perfect temperature compensation at two selected temperatures, and hence the value of either P5 or P7, is found by solving the quadratic equation:

$$R_x^2 + (R_{t1}^o + R_{t2}^o) R_x + R_{t1}^o R_{t2}^o = \frac{V(R_{t2}^o R_{t1}^o)}{i_{t1}^o - i_{t2}^o} \quad (6)$$

where $t_1$ and $t_2$ refer to the temperature at which the subscripted quantities are measured, and V is the voltage across the thermistor. This calculation must be performed twice, once to obtain the value of the setting for potentiometer P5 and once to obtain the value of the setting for potentiometer P7.

Voltage divider 116 utilizes a 1.2 Volt zener diode VR5 to supply a constant reference voltage for the monitor. The magnitude of the reference voltage may be varied through the use of potentiometer P9. Potential control circuit 118 receives the reference voltage from voltage divider 116 and supplies a voltage potential to the auxiliary electrode 12 through amplifier A7. Transistors Q13 and Q15 serve as the current booster 102.

Feedback from the reference electrode 14 is provided through amplifier A9.

The low power shut-off control 78 includes two comparators A21 and A23, permitting both the positive and negative supply voltage to be tracked separately. The positive input of each comparator is fed by the constant 1.2 volt reference voltage from voltage divider 116. Comparator A21 is set by means of potentiometer P11, which scales the positive supply voltage down to the magnitude of the reference voltage and supplies this scaled-down voltage to the negative input of comparator 21. Thus, whenever the positive supply voltage drops below a predetermined level as determined by the scale factor of potentiometer P11, comparator A21 will generate a pulse to activate transistor Q17. The activation of transistor Q17 in turn causes solid state relays 120 and 124 to respectively remove the $NO_2$ and NO indicating electrodes 58, 70 from the current measuring circuits 108, 110. Likewise, the negative supply voltage is scaled down by potentiometer P13, inverted and supplied to the negative input of comparator A23. When the negative supply drops to a predetermined level such that the negative input of comparator A23 falls below 1.2 volts (i.e., the reference voltage), comparator A23 generates a pulse which also activates transistor Q17 to energize solid state relays 120 and 124 and remove the $NO_2$ and NO indicating electrodes from the current measuring circuits. Capacitor C21 functions to hold the output of either comparator A21 or comparator A23 high in order to insure that the monitor will not immediately turn itself back on again following activation of transistor Q17. The output of transistor Q17 is additionally furnished to the monitor power supply 76. As will be explained more fully hereinbelow, whenever transistor Q17 is activated the power supply to the monitor is interrupted, thereby turning the monitor off.

The condition of the power supply may be visually displayed on the $NO_2$ indicating meter 82 by depressing the power supply test switch 128. Switch 128 functions to complete a circuit between power supply 76 and meter 82. A green stripe may be placed on the meter face to indicate the range of usable power supply voltages.

FIG. 8B illustrates a preferred embodiment of power supply 76. Ten 1.2 ampere hour nickel-cadmium cells 130 are connected in series to supply an operating potential through on-off switch 132 to positive and negative output terminals respectively indicated at 134 and 136. Relay coils K1 and K3 are energized in response to the activation of transistor Q17 in low power shut-off circuit 78 to remove the power supply from the remainder of the monitor circuitry whenever the positive or negative supply voltage becomes too low for monitor operation. If desired, the battery supply circuitry can be provided with a jack 138 for receiving the plug from a battery charging circuit (not shown), thus enabling batteries 130 to be recharged. Relays K1 and K3 can be reset only after plugging the battery charger into the power supply circuit, turning on-off switch 132 to the OFF position, and then turning the switch back to the ON position.

The digital timing circuit 80 for controlling the operation of the sample pump 38 is illustrated in detail in FIG. 8C. When MODE switch 140 is turned to CONTINUOUS, transistor Q19 is activated to turn sample pump 38 on. Zener diode VR7 and resistor R79 form a constant current source to supply the sample pump with a 40 mA current. When MODE switch 140 is placed in the MANUAL position, push button 142 must be depressed to activate the pump. Push button 142 triggers integrated circuit IC5 to output a pulse, the length of which is determined by the values of resistor R83 and capacitor C27. In the preferred embodiment, the circuit components can be chosen to provide a pumping time of approximately 60 seconds. A green light-emitting diode 144 connected in series with sample pump 38 to minimize current consumption turns on when the sample pump is operative.

For the sake of convenience, the values of all components employed in the construction of the preferred embodiment illustrated in FIGS. 8A–8C are listed in Table III.

TABLE III

Values of Circuit Components in FIGS. 8A, 8B and 8C

| Component | Value/Designation | Component | Value/Designation |
|---|---|---|---|
| C11 | 1N5305 | IC1 | RCA 4066 relay |
| CL3 | 1N5305 | IC3 | RCA 4066 relay |
| VR1 | 1N702 | IC5 | Fairchild 4528 mono |
| VR3 | 1N702 | K1 | Teledyne J422-9WL |
| VR5 | LM113 | K3 | Teledyne J422-9WL |
| VR7 | 1N41733 | P5 | 100KΩ Trimpot |
| Q5 | 2N5133 | P7 | 100KΩ Trimpot |
| Q7 | 2N5138 | P9 | 100KΩ Trimpot |
| Q9 | 2N5133 | P11 | 100KΩ Trimpot |
| Q11 | 2N5138 | P13 | 100KΩ Trimpot |
| Q13 | 2N5133 | CAL-1 | 50KΩ, Bourns 534 |
| Q15 | 2N5138 | CAL-3 | 10KΩ, Bourns 534 |
| Q17 | 2N5133 | ZERO-1 | 20KΩ, Bourns 534 |
| Q19 | 2N5133 | ZERO-3 | 20KΩ, Bourns 534 |
| A7 | CA340T | NULL | 50KΩ, Bourns 534 |
| A9 | CA31405 | C5 | 15 μf electrolytic |
| A11 | LM324 | C7 | 15 μf electrolytic |
| A13 | LM324 | C9 | 0.1 μf ceramic |
| A15 | LM324 | C11 | 0.1 μf ceramic |
| A17 | LM324 | C13 | 560pf ceramic |
| A19 | LM324 | C15 | 200pf ceramic |
| A21 | LM324 | C17 | 0.01 μf |
| A23 | LM324 | C19 | 0.01 μf |
| C21 | 50 μf electrolytic | R49 | 68KΩ |
| C23 | 20 μf electrolytic | R50 | 47KΩ |
| C25 | 50 μf electrolytic | R51 | 100Ω |
| C27 | 15 μf electrolytic | R53 | 47Ω |
| C29 | 15 μf electrolytic | R55 | 2.2KΩ |
| R17 | 100Ω | R57 | 100KΩ |
| R19 | 200KΩ | R59 | 100KΩ |
| R21 | 100KΩ | R61 | 10KΩ |
| R23 | 100KΩ | R63 | 100KΩ |
| R25 | 470Ω | R65 | 33KΩ |
| R27 | 9.1KΩ | R67 | 10KΩ |
| R29 | 49.1KΩ | R69 | 100KΩ |
| R31 | 100Ω | R70 | 10KΩ |
| R33 | 200KΩ | R71 | 150KΩ |
| R35 | 100KΩ | R73 | 5Ω |
| R37 | 100KΩ | R75 | 5Ω |
| R39 | 470Ω | R77 | 100Ω |
| R41 | 9.1KΩ | R79 | 75Ω |
| R43 | 49.1KΩ | R81 | 47Ω |
| R45 | 22KΩ | R83 | 10MΩ |
| R47 | 22KΩ | R85 | 100KΩ |
|  |  | R87 | 4.7KΩ |

INDUSTRIAL APPLICATION

There are numerous advantages to constructing an $NO/NO_2$ monitor in accordance with the foregoing specification. In particular, the ability to sense both NO and $NO_2$ concentrations in a single electrochemical cell fitted with two indicating electrodes eliminates the need for the multiple cell arrangement heretofore required in carrying out separate NO and $NO_2$ analyses. The reduction in number of cells results in a corresponding decrease in the complexity and bulk of the circuitry necessary to process indicating currents. Additional circuit reductions may be achieved in consequence of the fact that NO₂ may be measured with an indicating electrode held at constant potential, thereby eliminating the need for potential sequencing. Moreover, the measurement of $NO_2$ concentration at a cathodic potential, where a majority of possible interferences are electro-inactive, reduces the need for complex filtering systems in the monitor input section.

Figure 9:
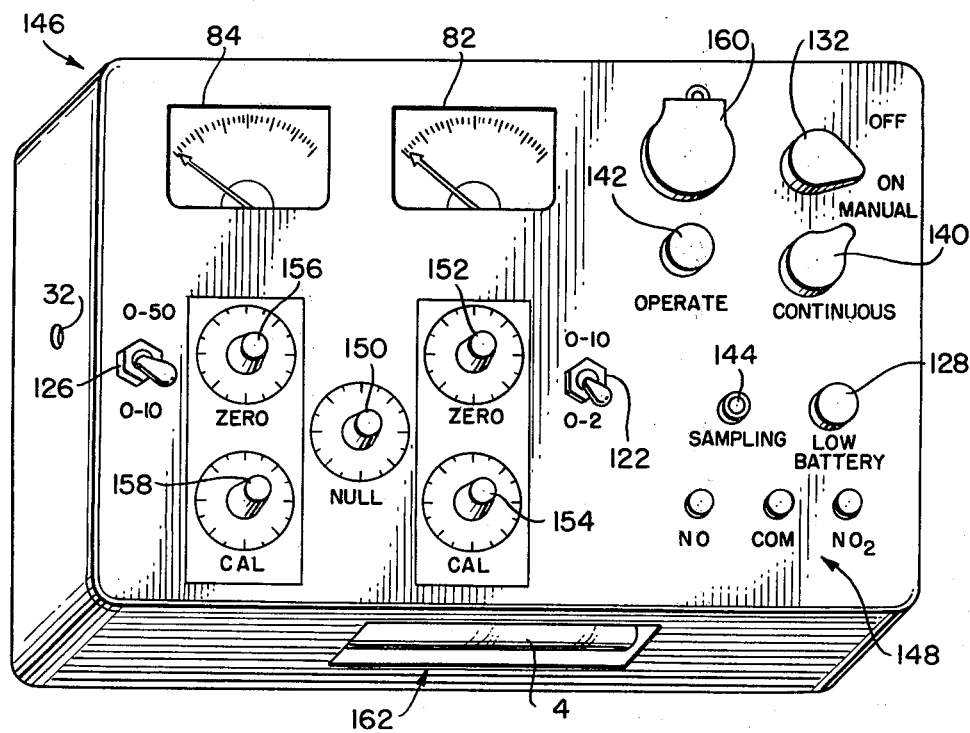
FIG. 9 is a perspective view of the exterior of a portable $NO/NO_2$ monitor constructed in accordance with the present invention.

As a net result of the various savings in size and power requirements achieved by the present invention, an $NO/NO_2$ monitor constructed in accordance with the foregoing specification is readily adapted for manufacture in a portable configuration, as generally illustrated at 146 in FIG. 9. Power is supplied to the monitor by turning on-off switch 132 to the ON Position. Thereafter, a sample stream of air is drawn into entry port 32 and passes through the monitor as determined by the position of MODE switch 140. It will be remembered that sample pump 38 operates continuously when MODE switch 140 is in the CONTINUOUS position, while push button 142 must be depressed to activate the sample pump when the MODE switch 140 is in the MANUAL position. Meters 82 and 84 are mounted to indicate respective concentrations of $NO_2$ and NO in the air sample. Range switch 122 is used to set the desired concentration range of $NO_2$ meter 82, while range switch 126 is used to set the desired concentration range of NO meter 84. The $NO_2$ and NO recorder output jacks REC-1 and REC-3 are indicated generally at 148. Zeroing knob 152 and calibration knob 154 control the adjustment of the ZERO-1 and CAL-1 potentiometers in $NO_2$ current measuring circuit 108. Zeroing knob 156 and calibration knob 158 similarly control the adjustment of potentiometers ZERO-3 and CAL-3 in NO current measuring circuit 110. Knob 150 is used to set the NULL potentiometer of compensating circuit 112. $NO_2$ indicating meter 82 may be used to supply a visual display of the condition of the power supply by depressing the power supply test switch 128, as previously described. In the event that the monitor battery supply needs to be recharged, protective cap 160 can be removed to uncover jack 138 (not shown in FIG. 9) for receiving a plug from a battery charging circuit.

Due to the fact that the $Cr_2O_3$ oxidant employed in oxidizing tube 4 of the $NO/NO_2$ monitor gradually changes color as the oxidizing ability thereof is lost, the need to replace the oxidant in the tube following prolonged usage of the monitor can be determined by visual inspection of the tube. To this end, a slot 162 can be formed in the side of the monitor and suitable connections can be made to enable the positioning of oxidizing tube 4 within slot 162, thereby permitting unobstructed viewing of the tube. Whenever the color of the oxidant indicates the need for replacement, the monitor operator follows the simple steps of removing tube 4, replacing the $Cr_2O_3$ oxidant, and re-connecting oxidizing tube 4 back in position in slot 162.

Only one embodiment of the present invention has been specifically shown and described herein. It is understood, however, that various additional changes and modifications in the form and detail of the gas monitoring apparatus illustrated above may be made of those skilled in the art without departing from the scope and spirit of the present invention. It is thus the intention of the inventors to be limited only by the following claims.

We claim:

1. An apparatus for simultaneously monitoring the presence of first and second members of a family of oxygen-containing gases in a sample of gas, said apparatus comprising:

(a) a first indicating means for generating a first indicating signal in response to the presence of the first member in the sample while forming a first gas mixture;

(b) means for receiving said first gas mixture from said first indicating means and for converting all of the second member present in said first gas mixture into the first member to form a second gas mixture;

(c) a second indicating means for receiving said second gas mixture from said converting means and for generating a second indicating signal in response to the presence of first member in said second gas mixture; and (d) circuit means for receiving said first and second indicating signals from said first and second indicating means and for respectively generating first and second output signals in response to said first and second indicating signals, said first output signal being representative of the amount of the first member present in the sample and said second output signal being representative of the amount of the second member present in the sample.

2. Apparatus as set forth in claim 1, wherein said first and second indicating means respectively include first and second electrodes mounted within an electrochemical cell.

3. Apparatus as set forth in claim 2, wherein said electrochemical cell includes an electrolyte in contact with said first electrode such that at least a portion of the first member present in the sample is electroreduced at said first indicating means to generate said first indicating signal in the form of an electrical signal while producing said first gas mixture, said first gas mixture producing said first gas mixture, said first gas mixture comprising electroreduction products, second member and unreduced first member, said electrolyte also contacting said second electrode such that the first member present in said second gas mixture is electroreduced at said second indicating means to generate said second indicating signal in the form of an electrical current.

4. Apparatus as set forth in claim 3, wherein said converting means includes an oxidizing means for converting all of the second member present in said first gas mixture into the first member to form said second gas mixture.

5. Apparatus as set forth in claim 4, wherein said electrolyte is an aqueous acid electrolyte.

6. Apparatus as set forth in claim 3, wherein said electrochemical cell also includes a reference electrode and an auxiliary electrode which form, together with said first and second electrode, a four electrode potentiostat.

7. Apparatus as set forth in claim 6, wherein said reference electrode comprises a glass element in contact with said electrolyte.

8. Apparatus as set forth in claim 3, wherein said circuit means includes a compensating means for removing from said second indicating signal the signal characteristics resulting from the presence in said first gas mixture of both unreduced first member and second member produced as a consequence of the electroreduction of the first member occuring in said first indicating means.

9. Apparatus as set forth in claim 8, wherein said compensating means subtracts a fractional amount of said first indicating signal from said second indicating signal to produce a difference signal.

10. Apparatus as set forth in claim 9, wherein said circuit means additionally includes a first amplifier means for amplifying said first indicating signal to generate said first output signal and a second amplifier means for amplifying said difference signal to generate said second output signal.

11. Apparatus as set forth in claims 1 or 2, wherein the first member is nitrogen dioxide and the second member is nitric oxide.

12. Apparatus as set forth in claims 3, 4, 5, 6, 7, 8, 9 or 10, wherein the first member is nitrogen dioxide and the second member is nitric oxide.

13. Apparatus as set forth in claim 12, wherein said aqueous acid electrolyte includes sulfuric acid.

14. Apparatus as set forth in claim 13, wherein said aqueous acid electrolyte comprises a mixture of sulfuric and sulfamic acids.

15. Apparatus as set forth in claim 12, wherein said first and second electrodes both include a hydrophilic porous supporting membrane having a first layer of gold coated thereon and a second layer of silver overlying said gold layer such that said second layer of silver contacts said electrolyte.

16. Apparatus as set forth in claim 15, wherein said hydrophilic porous supporting membrane is formed from Teflon.

17. Apparatus as set forth in claim 12, wherein said first and second electrodes operate at cathodic potentials.

18. Apparatus as set forth in claim 17, wherein the potentials of said first and second electrodes are held at −0.24 volts relative to said reference electrode.

19. An electrode means for contacting both a sample of gas and an aqueous electrolyte to electrochemically reduce nitrogen dioxide present in the sample, said electrode means including a hydrophilic porous supporting membrane having a first surface which contacts the aqueous electrolyte and a second surface which contacts the sample of gas, said first surface having a first layer of gold coated thereon and a second layer of silver overlying said first layer of gold.

20. An electrode means as set forth in claim 19, including a glass tube having an opening at one end thereof and said hydrophilic porous supporting membrane mounted across said opening, whereby said second surface is exposed to a sample of gas enclosed within said glass tube.

21. An electrode means as set forth in claim 20, wherein an electrical contact lead is connected to said first layer of gold to remove current generated during the electrochemical reduction of nitrogen dioxide.

22. Circuit means for providing first and second output signals in an apparatus in order to monitor the presence of first and second constitutents of a sample of gas, which apparatus includes electrochemical means for generating a first indicating signal having a characteristic resulting from the presence of the first constituent in the sample and a second indicating signal having a characteristic resulting from the combined presence of the first and second constitutents in the sample, said circuit means comprising:

(a) first amplifier means for amplifying the first indicating signal to provide said first output signal;

(b) compensating means for subtracting a fractional amount of the first indicating signal from the second indicating signal to produce a difference signal having a characteristic resulting only from the presence of the second constituent in the sample; and (c) second amplifier means for amplifying said difference signal to provide said second output signal.

23. Circuit means as set forth in claim 22, wherein said compensating means is connected between the output side of said first amplifier means and the input side of said second amplifier means.

24. Circuit means as set forth in claim 23, wherein said compensating means includes a potentiometer.

25. Circuit means as set forth in claim 22, including a power supply means for supplying an operating voltage to said circuit means.

26. Circuit means as set forth in claim 25, wherein said power supply means includes a low power shut-off means for interrupting the supply of said operating voltage from said power supply means to said circuit means and for preventing said circuit means from receiving the first and second indicating signals whenever the absolute value of said operating voltage falls below a predetermined level.

27. Circuit means as set forth in claim 26, wherein said low power shut-off means includes at least one comparator means for comparing the value of said operating voltage with a reference voltage having said predetermined level.

28. Circuit means as set forth in claim 25, wherein said power supply means includes an energy storage means.

29. Circuit means as set forth in claim 22, wherein said first and second amplifier means each includes a current booster means.

30. A method for simultaneously monitoring the presence of first and second members of a family of oxygen-containing gases in a sample of gas, said method comprising the steps of:

(a) electroreducing at least a portion of the first member in the sample to derive a first electrical signal while forming a first gas mixture comprising electroreduction products, unreduced first member and second member;

(b) oxidizing the second member in said first gas mixture to convert all of the second member present in said first gas mixture to the first member to form a second gas mixture;

(c) electroreducing at least a portion of the first member and in said second gas mixture to derive a second electrical signal; and (d) electronically processing said first and second electrical signals to generate first and second output signals respectively representative of the amount of the first and second members present in the sample.

31. A method as set forth in claim 30, wherein the first member is nitrogen dioxide and the second member is nitric oxide.

32. A method as set forth in claim 31, wherein nitrogen dioxide is electroreduced by contacting the nitrogen dioxide with an electrode structure which includes a metallic silver portion immersed in an aqueous acid electrolyte.

33. A method as set forth in claim 32, wherein said electrode structure is held at a cathodic potential relative to a predetermined reference level.

34. A method as set forth in claim 33, wherein said electrode structure is held at a potential of −0.24 volts relative to said predetermined reference level.

35. A method as set forth in claim 30, wherein the second member is oxidized by contacting the second member with $Cr_2O_3$.

36. A method for manufacturing an electrode capable of electroreducing nitrogen dioxide, said method comprising the steps of:
(a) stretching a hydrophilic porous membrane over an electrode support structure;
(b) applying a gold resinate over the surface of said hydrophilic porous membrane;
(c) heat curing the resinate until a coating of gold is formed on said hydrophilic porous membrane; and
(d) electroplating said hydrophilic porous membrane to form a coating of silver on the exposed surface of said coating of gold.

37. A method as set forth in claim 36, including the step of conditioning the coating of gold by immersing the hydrophilic porous membrane having said coating of gold formed thereon in a 1 M solution of $HClO_3$ and applying a current to said coating of gold.

38. A method as set forth in claim 37, wherein said current applied to said coating of gold is a square wave current alternating between $-50$ mA and $+50$ mA at a frequency of 0.1 Hz.

39. A method as set forth in claim 38, wherein said square wave current is applied to said coating of gold for at least eight hours and nitrogen gas is blown over the hydrophilic porous membrane while said square wave current is being applied.

40. A method as set forth in claim 36, wherein said steps of applying and heat curing said gold resinate are repeated to form a multi-coating layer of gold on said hydrophilic porous membrane.

41. A method as set forth in claims 36 or 40, wherein said gold resinate comprises 28% gold suspended in an organic matrix.

42. A method as set forth in claim 36, wherein said electroplating is accomplished by immersing the gold-coated hydrophilic porous membrane in a 0.1 M $AgNO_3$/1 M $HNO_3$ solution and potentiostating said coating of gold at 0.0 volts for 3 minutes.

43. An electrochemical means for detecting predetermined constituents in a sample of gas, said electrochemical means including:
(a) a cell structure enclosing a supporting electrolyte;
(b) an indicator electrode means mounted in said cell structure for generating an electrical signal in response to the presence of a predetermined atmospheric constituent, said indicator electrode means comprising a hydrophilic porous supporting membrane having a first surface which contacts said supporting electrolyte and a second surface which contacts the sample of gas, said first surface having a first layer of gold coated thereon and a second layer of silver overlying said first layer of gold; and
(c) a reference electrode means mounted in said cell structure for maintaining a reference potential relative to said indicating electrode means, said reference electrode comprising a glass element in contact with said supporting electrolyte.

* * * * *